United States Patent
Nishtalas et al.

(10) Patent No.: US 7,981,052 B2
(45) Date of Patent: *Jul. 19, 2011

(54) ENDOSCOPIC SUBMUCOSAL CORE BIOPSY DEVICE

(75) Inventors: Srinivas Nishtalas, Burlington, MA (US); Tim E. Ward, Bedford, IN (US); James S. Bates, Bloomington, IN (US); Stephane Gobron, Northbrook, IL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/544,933

(22) Filed: Oct. 10, 2006

(65) Prior Publication Data

US 2007/0123800 A1    May 31, 2007

Related U.S. Application Data

(63) Continuation of application No. 10/361,684, filed on Feb. 11, 2003, now Pat. No. 7,137,956, which is a continuation of application No. 09/801,746, filed on Mar. 9, 2001, now Pat. No. 6,551,254, which is a continuation of application No. 09/406,917, filed on Sep. 28, 1999, now Pat. No. 6,248,081.

(51) Int. Cl.
*A61B 10/00* (2006.01)

(52) U.S. Cl. ...................................... 600/567
(58) Field of Classification Search .......... 600/562, 600/564, 566–568; 606/167, 170, 113, 114, 606/127, 128, 79, 184, 185, 179; 408/205
See application file for complete search history.

(56) References Cited

U.S. PATENT DOCUMENTS

| | | | |
|---|---|---|---|
| 2,606,615 A * | 8/1952 | Pevey et al. | 408/205 |
| 3,902,498 A | 9/1975 | Niederer | |
| 4,368,734 A | 1/1983 | Banko | |
| 4,457,313 A | 7/1984 | Alter | |
| 4,651,752 A | 3/1987 | Fuerst | |
| 4,766,907 A | 8/1988 | de Groot et al. | |
| 4,781,202 A | 11/1988 | Janese | |
| 4,893,635 A | 1/1990 | de Groot et al. | |
| 4,913,143 A * | 4/1990 | Oloff et al. | 606/170 |
| 4,926,877 A | 5/1990 | Bookwalter | |
| 4,966,162 A | 10/1990 | Wang | |

(Continued)

FOREIGN PATENT DOCUMENTS

AU        1844397 A    8/1997

(Continued)

*Primary Examiner* — Max Hindenburg
*Assistant Examiner* — Brian Szmal
(74) *Attorney, Agent, or Firm* — Finnegan, Henderson, Farabow, Garrett & Dunner LLP

(57) ABSTRACT

An embodiment of the invention includes a device for collecting body tissue. The device may include an inner member comprising a hollow portion to collect body tissue and a distal end configured to both penetrate body tissue and define an opening of the hollow portion. The device may further include an outer member, co-axially and slidably disposed around the exterior of the inner member, comprising a distal end portion. The distal end portion of the outer member may be configured to penetrate body tissue, prevent body tissue from exiting the hollow portion of the inner member, and allow the distal end of the inner member to extend beyond the distal end of outer member. The opening of the hollow portion of the inner member may be disposed in a plane that is not perpendicular to the longitudinal axis of the inner member.

24 Claims, 20 Drawing Sheets

U.S. PATENT DOCUMENTS

| | | |
|---|---|---|
| 5,056,529 A | 10/1991 | de Groot |
| 5,127,419 A | 7/1992 | Kaldany |
| 5,133,360 A | 7/1992 | Spears |
| 5,146,928 A | 9/1992 | Esser |
| 5,267,572 A | 12/1993 | Bucalo |
| 5,353,807 A | 10/1994 | DeMarco |
| 5,394,887 A | 3/1995 | Haaga |
| 5,427,115 A | 6/1995 | Rowland et al. |
| 5,462,062 A | 10/1995 | Rubinstein et al. |
| 5,462,063 A | 10/1995 | Kist et al. |
| 5,511,556 A | 4/1996 | DeSantis |
| 5,526,822 A | 6/1996 | Burbank et al. |
| 5,535,756 A | 7/1996 | Parasher |
| 5,573,008 A | 11/1996 | Robinson et al. |
| 5,595,186 A | 1/1997 | Rubinstein et al. |
| 5,669,923 A | 9/1997 | Gordon |
| 5,792,166 A | 8/1998 | Gordon et al. |
| 5,823,971 A | 10/1998 | Robinson et al. |
| 5,827,305 A | 10/1998 | Gordon |
| 5,857,982 A | 1/1999 | Milliman et al. |
| 5,885,226 A | 3/1999 | Rubinstein et al. |
| 5,910,121 A | 6/1999 | Paolo et al. |
| 6,007,497 A | 12/1999 | Huitema |
| 6,248,081 B1 | 6/2001 | Nishtalas et al. |
| 6,551,254 B2 | 4/2003 | Nishtalas et al. |
| 7,137,956 B2 * | 11/2006 | Nishtalas et al. ............ 600/567 |

FOREIGN PATENT DOCUMENTS

| | | |
|---|---|---|
| AU | 6654898 A | 9/1998 |
| CA | 1185491 A | 4/1985 |
| CA | 2172130 A | 3/1995 |
| CA | 2172132 A | 3/1995 |
| CA | 2172131 A | 4/1995 |
| CA | 2244072 A | 7/1997 |
| EP | 0720440 A | 7/1996 |
| EP | 0720442 A | 7/1996 |
| EP | 0722287 A | 7/1996 |
| EP | 0955913 A | 11/1999 |
| JP | 9502898 T | 3/1997 |
| JP | 9502909 T | 3/1997 |
| JP | 9504451 T | 5/1997 |
| JP | 2000503869 | 4/2000 |
| WO | WO 9319675 A | 10/1993 |
| WO | WO 9508291 A | 3/1995 |
| WO | WO 9508292 A | 3/1995 |
| WO | WO 9508946 A | 4/1995 |
| WO | 9726835 A | 7/1997 |
| WO | 9835615 A | 8/1998 |

* cited by examiner

ENDOSCOPIC SUBMUCOSAL CORE BIOPSY DEVICE

This is a continuation application of U.S. patent application Ser. No. 10/361,684, filed Feb. 11, 2003 now U.S. Pat. No. 7,137,956, which is continuation application of U.S. patent application Ser. No. 09/801,746, filed Mar. 9, 2001 now U.S. Pat. No. 6,551,254, which is a continuation application of U.S. patent application Ser. No. 09/406,917, filed Sep. 28, 1999 now U.S. Pat. No. 6,248,081, the entirety of all of which are incorporated herein by reference.

BACKGROUND OF THE INVENTION

1. Field of the Invention

The present invention relates to surgical instruments and, particularly, to an instrument for biopsy sampling of tissue. Still more particularly, the present invention relates to an endoscopic biopsy instrument that obtains core biopsy samples and integrates two or more biopsy-sampling modalities.

2. Background of Related Art

Biopsy is the removal and study of body tissue for medical diagnosis. Typically, physicians obtain biopsy samples in order to detect abnormalities such as cancer and determine the extent to which cancerous tissue has spread. They use various biopsy instruments to acquire tissue samples from different areas of the body. Many current biopsy instruments, however, cannot retrieve full core samples of tissue, do not provide versatility in sampling methods, or are overly intricate in design and manufacture.

During a biopsy tissue-sample procedure performed on a body lumen, a physician generally uses an endoscope to provide a passageway for entry of the biopsy instrument into the body. Having thus secured access to the biopsy site, the physician uses some device to extract a tissue sample from the wall of the target body lumen. Usually, the walls of body lumen, such as the esophagus, the gastrointestinal tract, or the urinary tract, have three layers: the surface mucosal or epithelial layer comprised of mucus; the submucosal layer, which is below the mucosal layer; and the muscle layer. Many current biopsy devices can only take tissue from the surface mucosal layer and also cannot retrieve full core samples.

In many situations, physicians may desire full core samples because, with larger cross-sections of tissue types, they can more accurately determine the extent to which cancer has spread. It is also desirable to obtain full, clean core samples that have not been crushed by devices penetrating into tissue. Moreover, it may be desirable to obtain a full core sample without having to penetrate past a desired depth of tissue in order to obtain a corresponding desired depth of core sample. It would be preferable to insert a biopsy needle only as far as necessary to obtain a full core sample to minimize trauma to the patient.

Further, many current devices lack versatility. Many devices today extract tissue samples through aspiration, brush cytology, or pinch biopsy. In the case of aspiration, a physician inserts a very fine needle into the wall of the target tissue and draws fluid, typically saline, through the needle. The physician thus collects some surface tissue cells. In the case of brush cytology, a physician introduces a brush through the lumen of the endoscope to collect tissue cells by scraping the surface of the target site. In the case of pinch biopsy, a physician inserts a bioptome, having a pair of opposed jaw cups, through the lumen of the endoscope, to the tissue site. The physician may then close the jaws around the target surface and pinch away a sample from the surrounding tissue.

Typically, current devices may employ only one of these methods to obtain tissue samples. Thus, a physician who desires tissue samples obtained through both aspiration and brush cytology, for example, must insert one instrument, take a sample, retrieve the instrument, insert a second instrument, take a second sample, and then retrieve the second instrument. Such practice is time consuming and leads to procedural inefficiency.

Many current instruments also have an overly complex design. Devices that might otherwise fulfill one of the aforementioned needs, such as the need to capture core samples, for example, often employ complex cutting mechanisms held in sheaths or housings requiring very exact tolerances.

In light of the foregoing, there exists a need for a biopsy tissue-sampling device that effectively obtains a full core tissue sample, accommodates multiple sampling modes, and is simple in design and inexpensive to manufacture.

SUMMARY OF THE INVENTION

It is therefore an object of the invention to provide a surgical instrument that is able to obtain a full core biopsy tissue sample with minimal trauma to the patient.

It is a further an object of the invention to provide a surgical instrument that integrates two or more biopsy tissue sampling modalities.

It is another object of the invention to provide a surgical instrument that integrates three biopsy tissue sampling modalities.

Additional objects and advantages of the invention will be set forth in the description which follows and, in part, will be obvious from the description or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises an instrument for collecting body tissue, comprising: a needle having an axial center, an exterior surface, a hollow interior, a distal end and a proximal end, wherein the distal end is capable of penetrating body tissue; a flexible cutting extension coaxially and slidably disposed around the exterior surface of the needle, the cutting extension including a blade surface having a cutting edge wherein the blade surface is biased toward the axial center of the needle such that the cutting extension moves toward the axial center of the needle when urged past the distal end of the needle and the edge cuts tissue located at the distal end of the needle and the blade surface covers the distal end of the needle so that tissue that has entered the hollow interior of the needle is trapped in the hollow interior of the needle.

In a preferred embodiment, the cutting extension comprises a symmetrical arrangement of blade surfaces biased toward the axial center of the needle.

In another preferred embodiment, the cutting extension includes a plurality of blade surfaces biased toward the axial center of the needle.

In another preferred embodiment, the blade surface of the flexible cutting extension forms an opening and at least part of the surface forming the opening forms the cutting edge.

In another preferred embodiment, the instrument further comprises: a first tubular member having a proximal end and a distal end connected to the proximal end of the needle; a second tubular member coaxially disposed around the first tubular member, the second tubular member having a proximal end and a distal end connected to the proximal end of the cutting extension; and a handle mechanism connected to the proximal ends of the first and second tubular members, the handle mechanism having a housing and a means for extending the cutting extension beyond the distal end of the needle.

In another preferred embodiment, the means for extending the cutting extension comprises a resilient member connected between the handle housing and the second tubular member for extending the cutting extension connected to the second tubular member distally beyond the distal end of the needle.

In still another preferred embodiment, the means for extending the cutting extension comprises a first hub connected to the first tubular member and a second hub connected to the second tubular member, the second hub slidable relative to the first hub to extend the cutting extension relative to the needle.

In another preferred embodiment, the instrument further comprises a third tubular member coaxially disposed around the first and second tubular members and having a proximal end connected to the handle housing.

In yet another preferred embodiment, the instrument further comprises a fourth tubular member disposed within the third tubular member a brush coaxially disposed in the fourth tubular member.

In another preferred embodiment, the instrument further comprises a brush coaxially disposed in the first tubular member.

In another preferred embodiment, the proximal end of the first tubular member is connected to a vacuum source for cell aspiration.

In another preferred embodiment, an instrument for collecting body tissue is provided, comprising: a tubular cutting member having an exterior surface, a proximal end and a distal end capable of penetrating body tissue; a flexible cutting extension coaxially and slidably disposed around the exterior surface of the cutting member, the flexible cutting extension having a proximal end and a distal end capable of cutting tissue located at the distal end of the cutting member and covering the distal end of the cutting member so that tissue that has entered the needle is retained in the cutting member; a first tubular member connected to the cutting member; a second tubular connected to the cutting extension; a handle mechanism connected to the first and second tubular members such that the flexible cutting extension may be extended beyond the distal end of the cutting member.

In another preferred embodiment, an instrument for collecting body tissue is provided, comprising: a needle having an axial center, an exterior surface, a hollow interior, a proximal end and a distal end capable of penetrating body tissue, a flexible cutting extension coaxially and slidably disposed around the exterior surface of the needle, the flexible cutting extension including at least a blade surface having a cutting edge and being biased toward the axial center of the needle such that the flexible cutting extension moves toward the axial center of the needle when urged past the distal end of the needle and the edge cuts tissue located at the distal end of the needle and the blade surface covers the distal end of the needle; a first tubular member having a proximal end and a distal end connected to the proximal end of the needle; a second tubular member coaxially disposed around the first tubular member, the second tubular member having a proximal end and a distal end connected to the proximal end of the cutting extension and being moveable relative to the first tubular member to provide relative movement between the needle and the flexible cutting extension.

It is to be understood that both the foregoing general description and the following detailed description are exemplary and explanatory and are not restrictive of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention.

DETAILED DESCRIPTION

Figure 1:
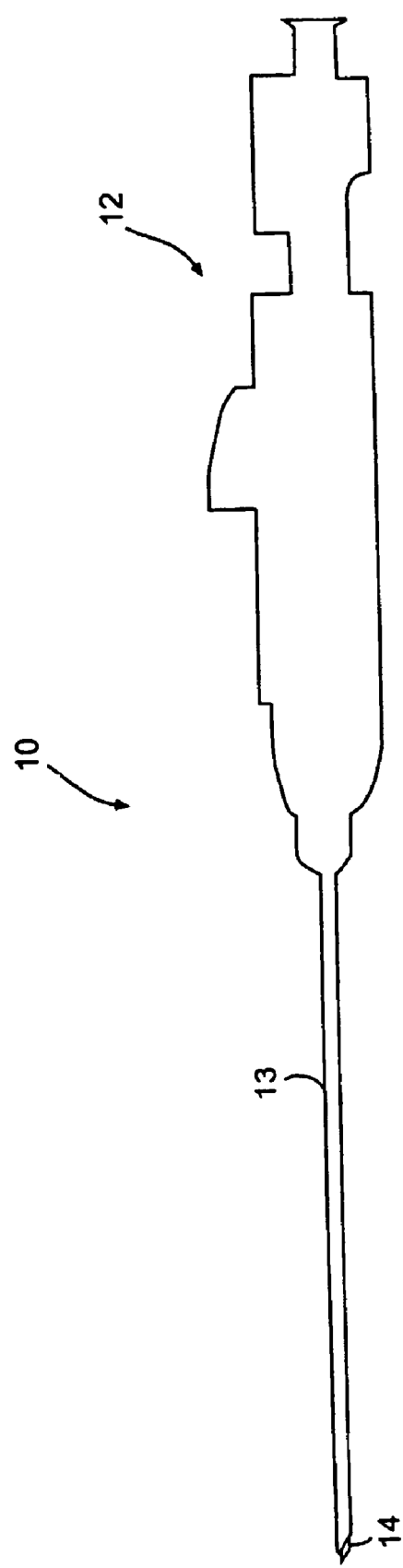
FIG. 1 is a side elevation view of an endoscopic bioptome according to a preferred embodiment of the present invention.

Reference will now be made in detail to the present preferred embodiments of the invention, examples of which are illustrated in the accompanying drawings. Wherever possible the same reference numbers are used in the drawings and the description to refer to the same or like parts.

The present invention is directed to a surgical instrument, particularly an endoscopic instrument for obtaining a biopsy of submucosal tissue. The instrument described in detail below uses a unique end effector to obtain full core biopsy samples and integrates multiple modalities of biopsy tissue sampling. The instrument integrates aspiration and brush cytology with full core biopsy sampling.

The instrument according to the present invention is shown generally at 10 in FIG. 1. Instrument 10 includes three main sections: a handle assembly 12 at its proximal end; an end effector assembly 14 at its distal end; and a tubular section 13 extending between handle 12 and end effector assembly 14. End effector 14 generally includes inner and outer coaxial cutting members. Tubular section 13 and end effector 14 may be deployed to the tissue site through the working channel of an endoscope or other delivery mechanism.

Figure 2:
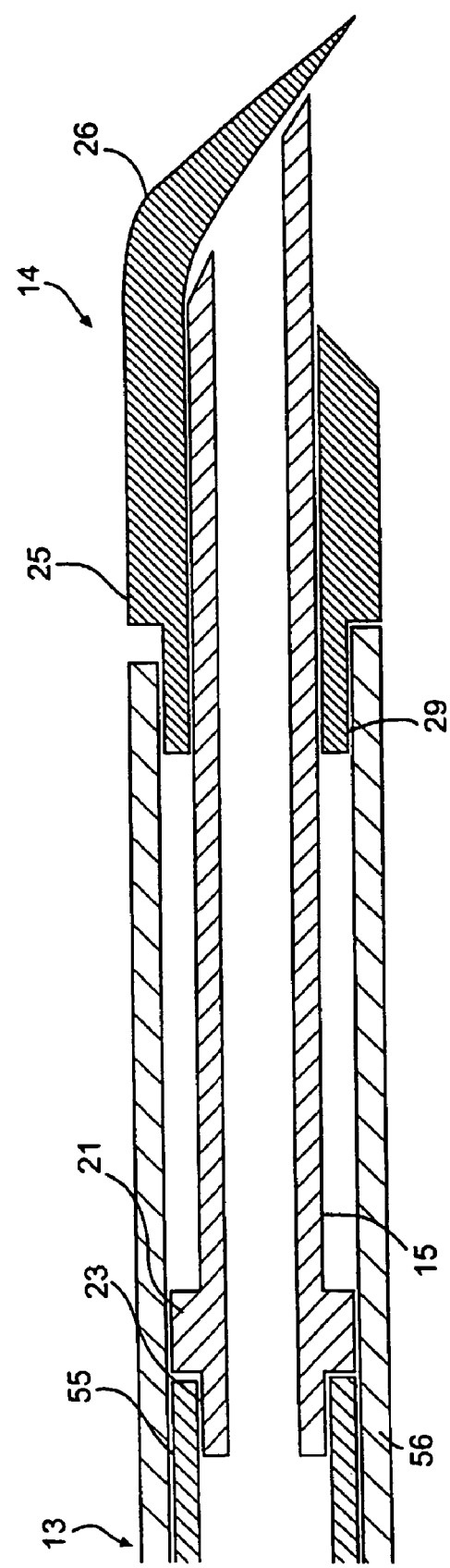
FIG. 2 is a sectional side view of an end effector cutting mechanism according to the present invention.
Figure 3A:
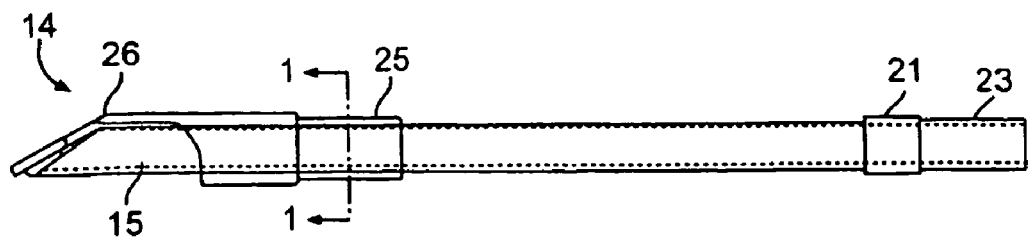
FIG. 3A is a side view of an end effector cutting mechanism according to the present invention.
Figure 3B:
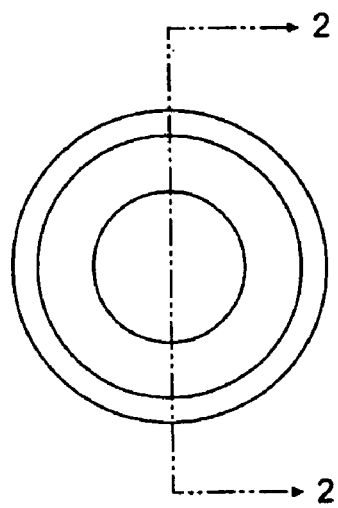
FIG. 3B is a cross-sectional bottom, end view of the end effector cutting mechanism of FIG. 3A taken along line 1-1.
Figure 3C:
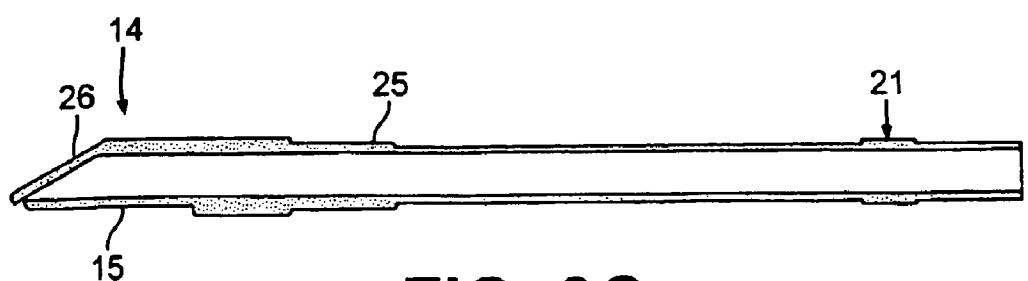
FIG. 3C is a cross-sectional side view of the end effector cutting mechanism of FIG. 3A taken along the line 2-2 shown in FIG. 3B.
Figure 3D:
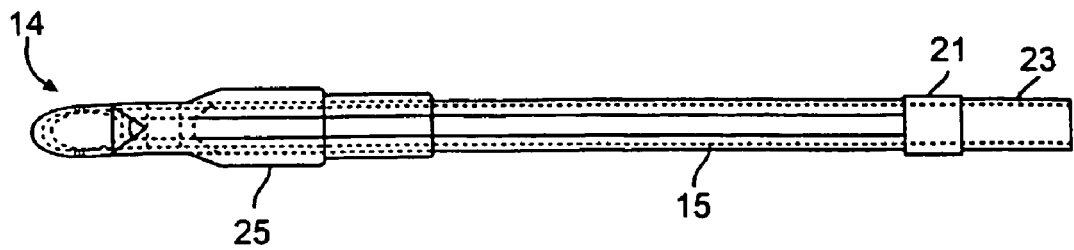
FIG. 3D is a top view of the end effector cutting mechanism of FIG. 3A.
Figure 3E:
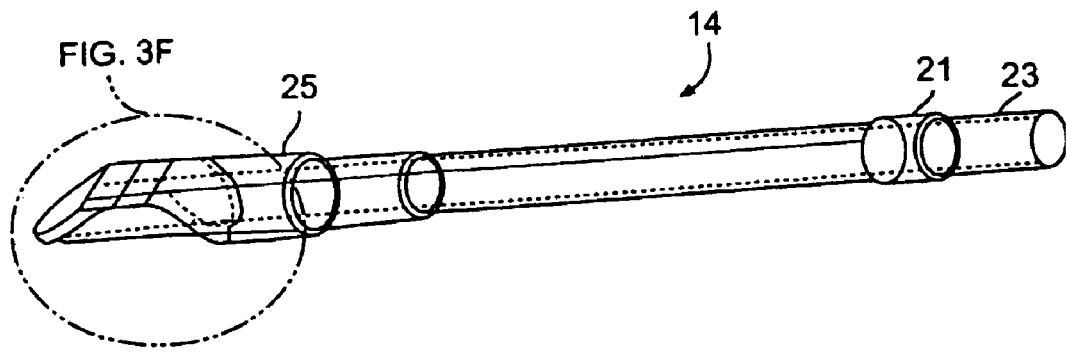
FIG. 3E is an side elevational view of the end effector cutting mechanism of FIG. 3A.
Figure 3F:
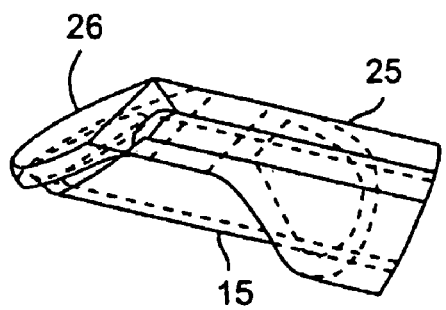
FIG. 3F is an enlarged view of the distal end of the end effector cutting mechanism of FIG. 3E.
Figure 4A:
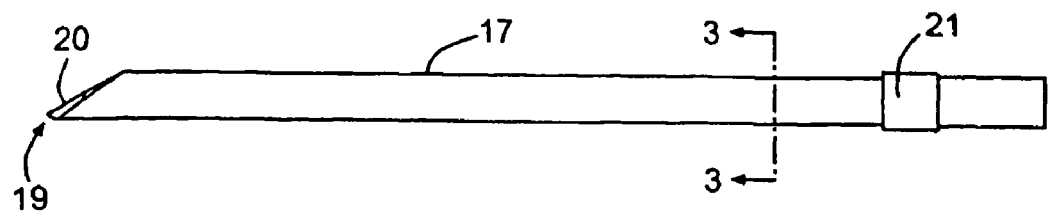
FIG. 4A is a side view of a needle portion of an end effector cutting mechanism according to the present invention.
Figure 4B:
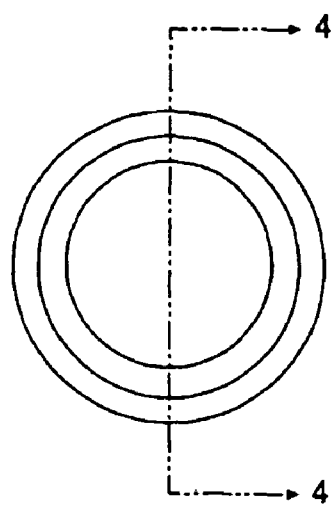
FIG. 4B is a cross-sectional bottom, end view of the needle of FIG. 4A taken along the line 3-3.
Figure 4C:
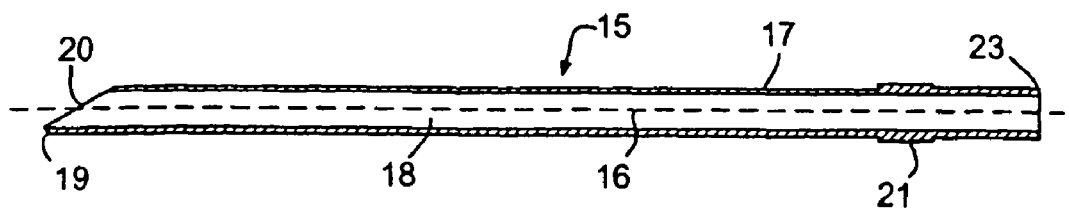
FIG. 4C is cross-sectional side view of the needle of FIG. 4A taken along the line 4-4 shown in FIG. 4B.
Figure 4D:
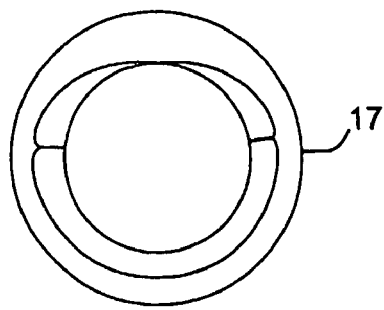
FIG. 4D is a cross-sectional top, end view of the needle of FIG. 4A.
Figure 4E:
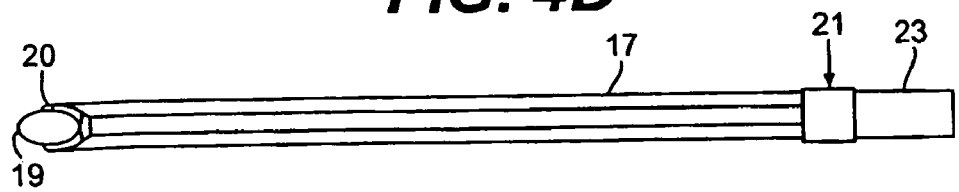
FIG. 4E is a bottom elevational view of the needle of FIG. 4A.
Figure 4F:
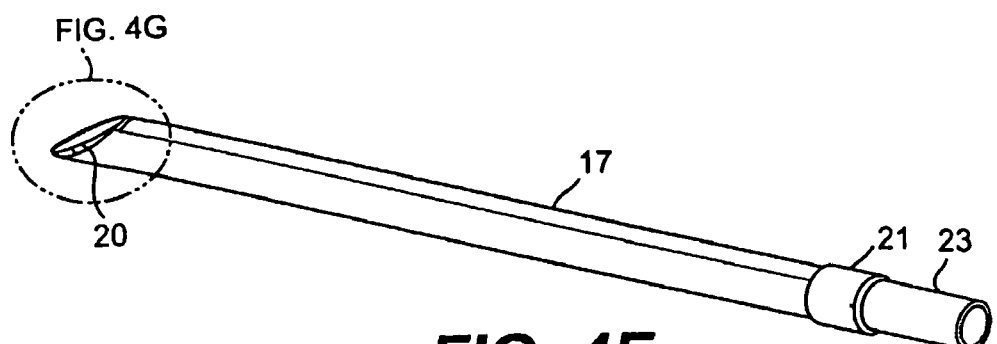
FIG. 4F is a side elevational view of the needle of FIG. 4A.
Figure 4G:
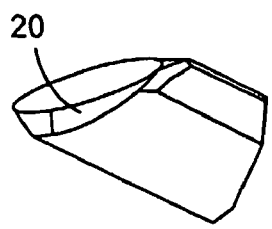
FIG. 4G is an enlarged view of the distal end of the needle of FIG. 4G.
Figure 5A:
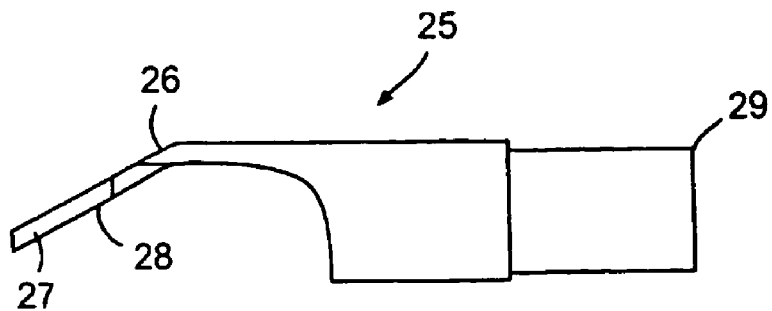
FIG. 5A is a side view of an outer cutting mechanism of an end effector cutting mechanism of the present invention.
Figure 5B:
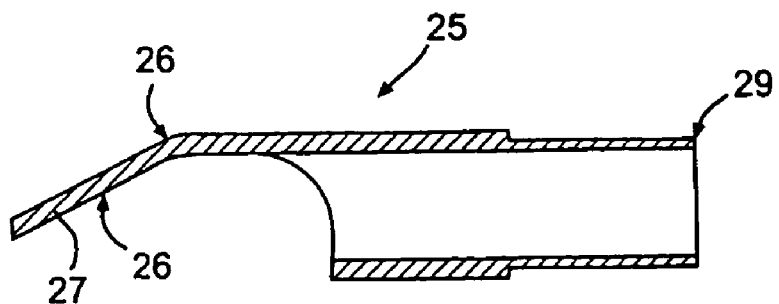
FIG. 5B is a cross-sectional side view of the outer cutting mechanism of FIG. 5A.
Figure 5C:
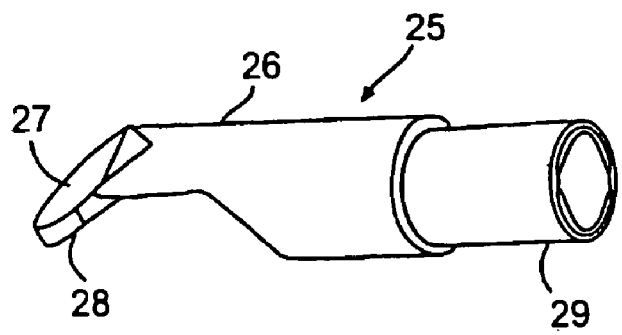
FIG. 5C is side elevational view of the outer cutting mechanism of FIG. 5A.
Figure 5D:
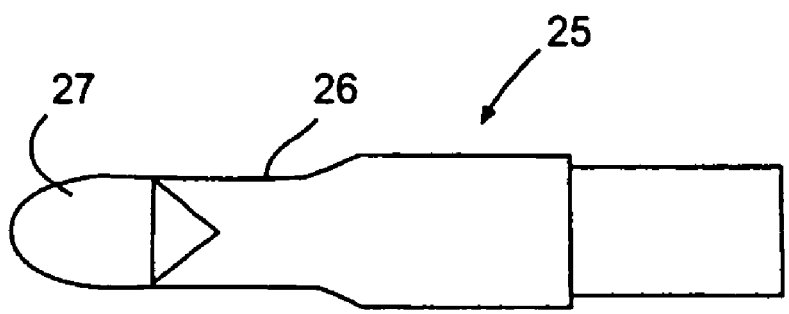
FIG. 5D is top elevational view of the outer cutting mechanism of FIG. 5A.
Figure 5E:
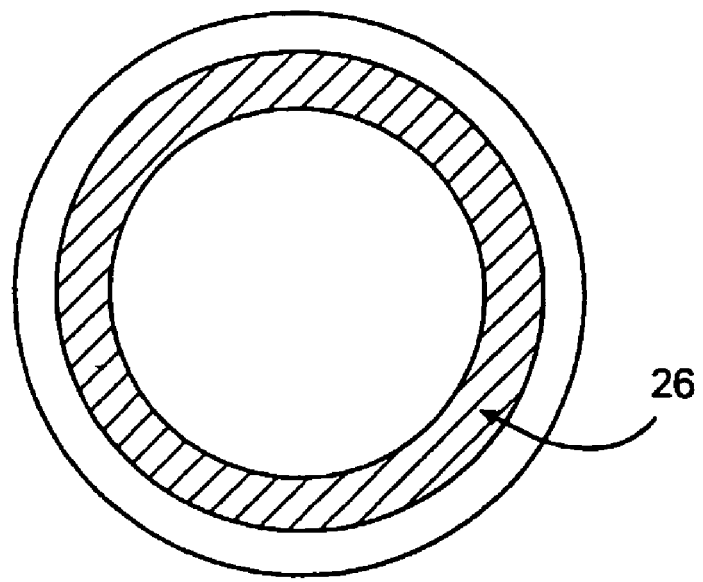
FIG. 5E is a cross-sectional end view of the outer cutting mechanism of FIG. 5A.

As illustrated in FIGS. 2 and 3A-3F, end effector 14 includes an inner cutting mechanism preferably consisting of a needle 15 having a sharpened distal end for penetrating tissue and an outer cutting mechanism 25 biased inwardly to cut tissue located within the interior of needle to retain the tissue within the interior of needle 15. FIGS. 3A-3F illustrate various views of end effector 14. FIG. 3F illustrates an enlarged view of the distal end of end effector 14.

As embodied herein, and as illustrated in FIGS. 4A-4G, needle 15 has an axial center 16, an exterior surface 17, a hollow interior 18, a proximal end 23, and a distal end 19 capable of penetrating body tissue. At least a portion, and preferably all, of the distal end of needle provides a sharpened cutting surface 20. As needle 15 is advanced into body tissue, sharpened distal end 19 cuts tissue that enters the hollow interior 18 of needle 15 to provide a full core biopsy sample. In the embodiment shown in FIGS. 4A-4G, cutting surface 20 of needle 15 is formed to a pointed, angular, cutting surface.

Needle 15 may also be provided with a hub 21 toward its proximal end 23. Hub 21 serves as a stop for a catheter or other tubular member received on the proximal end 23 of needle 15 and for outer cutting mechanism 25. The end of a catheter or other tubular member, which forms part of tubular section 13, may abut the hub portion 21 of needle 15 and may be retained on the needle by adhesive or other fixing mechanism. Needle 15 may also be formed integrally with a catheter or other tubular member. Needle 15 is preferably a flexible needle, such as a flexible sclerotherapy needle, but may also be rigid. While the inner cutting mechanism has been described as a needle, it is not limited to such and it should be recognized that any suitable tubular member having a sharpened distal end for penetrating tissue may be used.

In the embodiment shown in FIGS. 5A-5E, outer cutting mechanism 25 includes a flexible cutting extension 26, coaxially and slidable disposed around the exterior surface 17 of needle 15. Cutting extension 26 includes a proximal portion 29, and a distal blade surface 27 having a sharpened edge 28. Sharpened edge 28 extends along at least a portion, and preferably all, of the perimeter of blade surface 27. Cutting extension 26 is biased radially inward toward the axial center 16 of needle 15 such that cutting extension 26 moves toward the axial center of needle 15 when it is extended beyond the distal end of needle 15. Blade surface 27 also covers the distal end of needle 15 when it is extended such that tissue that has entered needle 15 is trapped within the hollow interior 18 of needle 15. Cutting extension 26 and blade 27 are preferably made from a metallic alloy, either machined, cast, or stamped to obtain the desired shape and structure. It should be recognized that other suitable materials may be used.

Proximal portion 29 of cutting mechanism 25, preferably has a reduced diameter for receiving the end of a catheter or other tubular member, which forms part of tubular section 13. The tubular member may be retained on the proximal end portion 29 by adhesives or other fixing mechanism. When cutting extension 26 is disposed over needle 15, proximal portion 29 may abut hub portion 21 on needle 15 when cutting extension 26 is in the retracted position and needle cutting surface 20 is exposed. In this instance, the hub portion 21 acts as a back stop mechanism limiting rearward movement of the outer cutting mechanism. Alternatively, a tubular member may be connected to the cutting mechanism through a float as will be described in connection with FIGS. 7A-7D.

Figure 6:
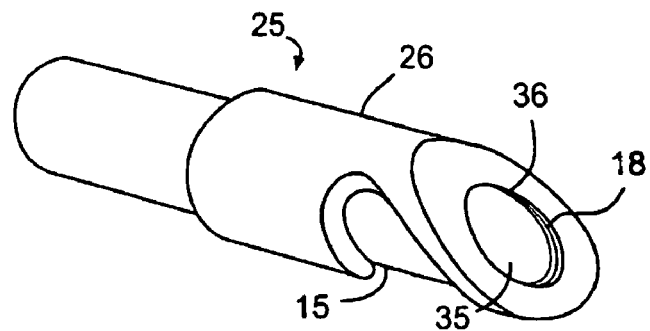
FIG. 6 is a side elevational view of an end-effector cutting mechanism according to another embodiment of the present invention.

As shown in FIG. 6, cutting extension 26 may alternatively be provided with a circular hole 35 corresponding to the opening formed in the distal end of needle 15. Hole 35 has a cutting surface 36, extending along at least a portion, and preferably the entire, circumference surface of hole 35. In operation, cutting extension 26 is extended over needle 15 such that hole 35 allows access to the hollow interior 18 of needle 15. Instrument 10 may then be advanced into the tissue site to be sampled and needle cutting surface 20 and/or cutting surface 36 of hole 35 cuts the tissue as the instrument is advanced causing the tissue to enter the hollow interior 18 of the needle 15. Cutting extension 26 may then be retracted causing cutting surface 36 of hole 35 to cut the tissue at the distal end of needle 15 trapping the tissue sample in the hollow interior 18 of needle 15. Alternatively, cutting extension 26 may be further extended, causing cutting surface 36 of hole 35 to cut the tissue at the distal end of the needle 15.

Figure 9A:
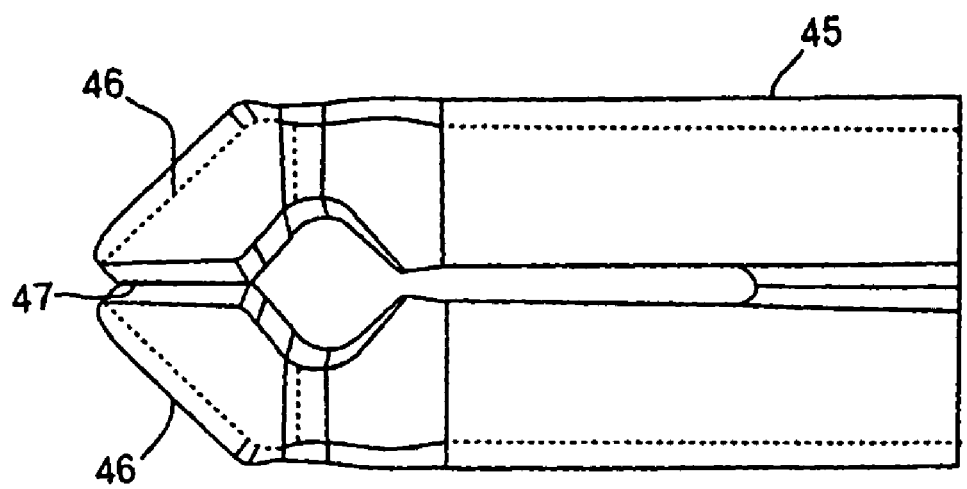
FIG. 9A is a side view of a cutting extension portion of an end effector cutting mechanism according to the present invention.
Figure 9B:
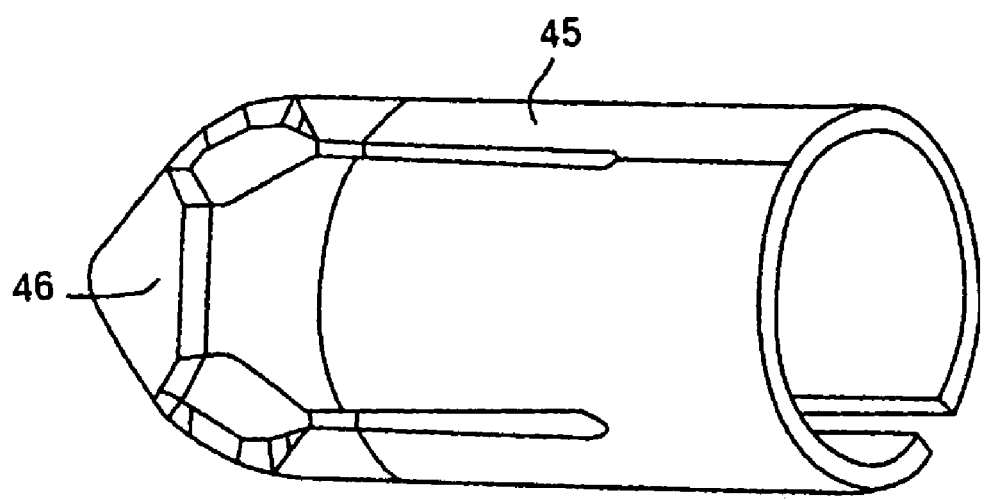
FIG. 9B is an elevation side view of the cutting extension of FIG. 9A.
Figure 9C:
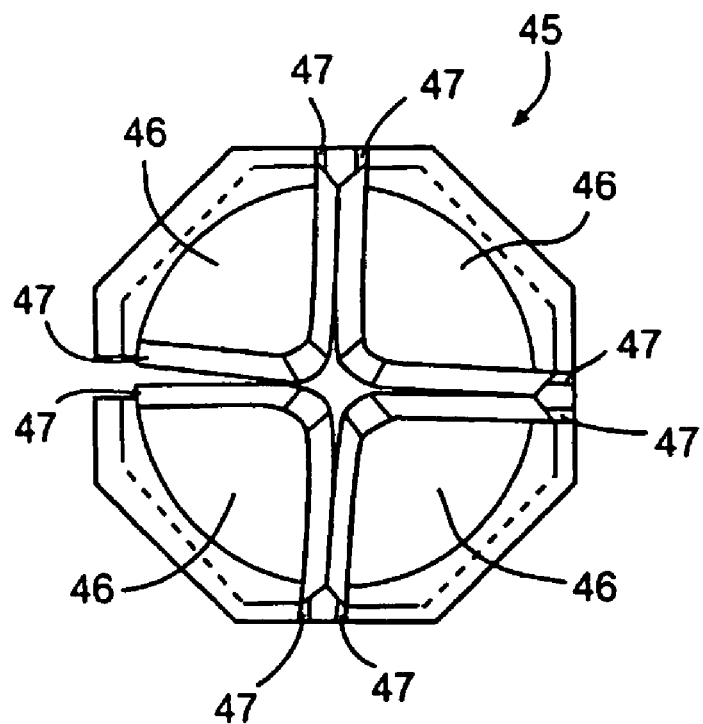
FIG. 9C is a top end view of the cutting extension of FIG. 9C.
Figure 9D:
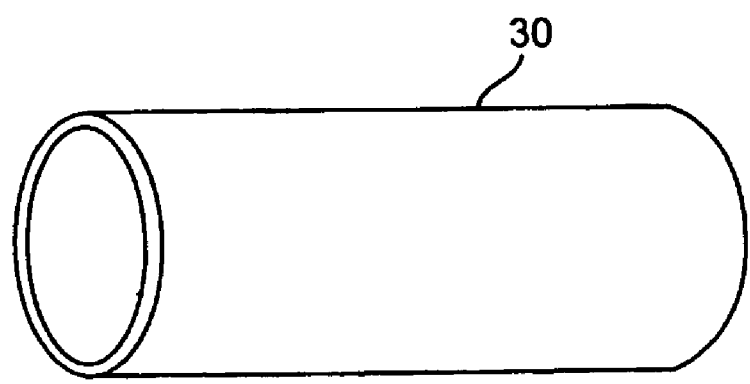
FIG. 9D is a side elevational view of a float portion of an end effector cutting mechanism according to the present invention.

Another end effector cutting mechanism is shown in FIGS. 7A-7D, 8A-8C, and 9A-9D. As shown in these figures, needle 15 includes sharpened distal end portion 40 having cutting surface 41. Cutting surface 41 preferably forms a wavy conical-shaped surface having rounded roots and preferably extends along the entire distal end portion 40. Outer cutting mechanism 25 includes cutting extension 45. Cutting extension 45 includes multiple cutting surfaces, shown here as four cutting blade surfaces 46 having edges 47, arranged radially around an axial center 48 of cutting extension 45. Blade surfaces 46 are all biased toward the axial center 16 of needle 15. Blade surfaces 46 are flexible and move toward the axial center 16 of needle 15 when cutting extension 45 is extended beyond the distal end 40 of needle 15. Blade surfaces 46 also cover the distal end 40 of needle 15 so that tissue that has entered needle 15 is trapped in the hollow interior 18 of needle 15. As shown in FIGS. 9A-9C, edges 47 of blade surfaces 46 preferably contact each other to cover the opening of the hollow interior 18 of needle 15. Cutting extension 45 and blade surfaces 46 are preferably made from thin metallic material, preferably stamped and formed, but possibly machined and cast, into a circular tubular shape. It should be recognized that other suitable materials may be used. While cutting extension 45 is illustrated with four cutting surfaces it should also be recognized that fewer or additional cutting surfaces could be used.

Figure 7A:
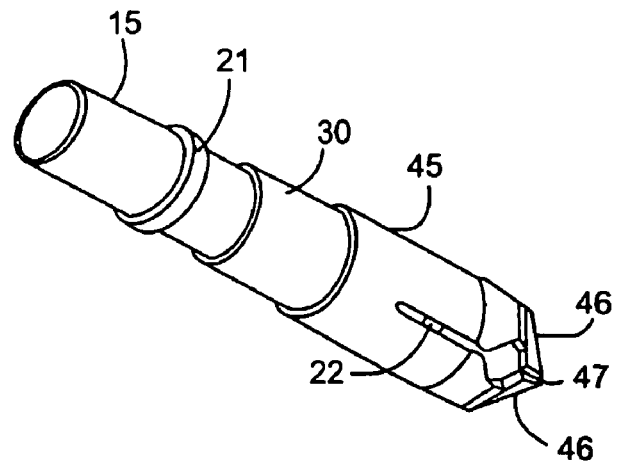
FIG. 7A is a side elevational view of an end effector cutting mechanism according to another embodiment of the present invention.
Figure 7B:
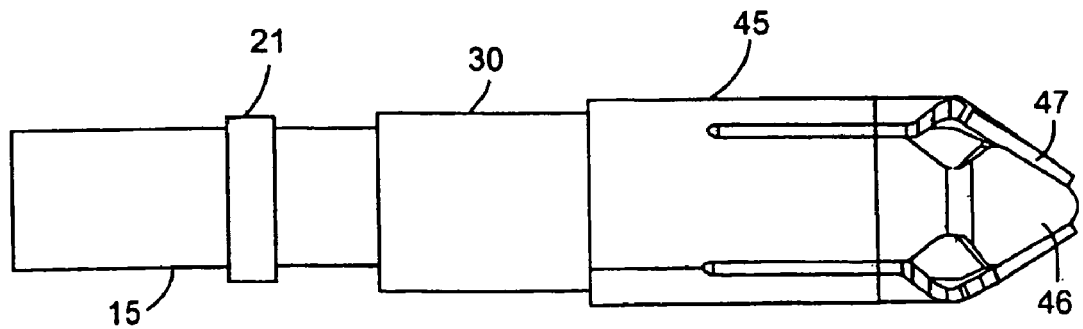
FIG. 7B is a side view of the end effector cutting mechanism of FIG. 7A.
Figure 7C:
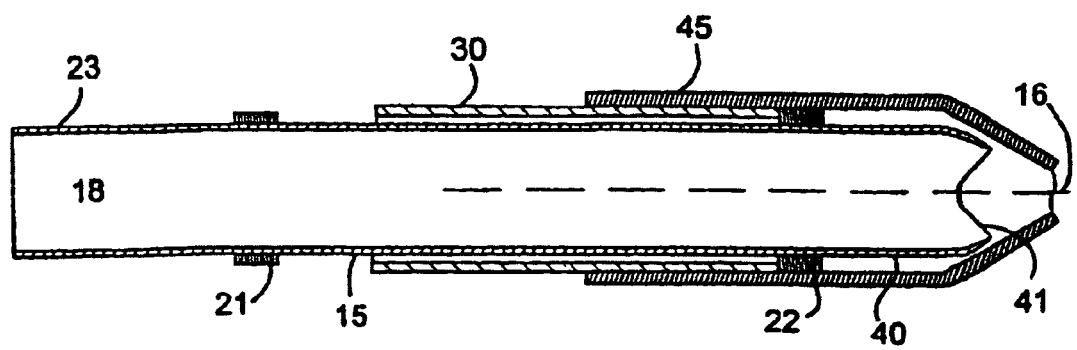
FIG. 7C is a cross-sectional side view of the end effector cutting mechanism of FIG. 7A.
Figure 7D:
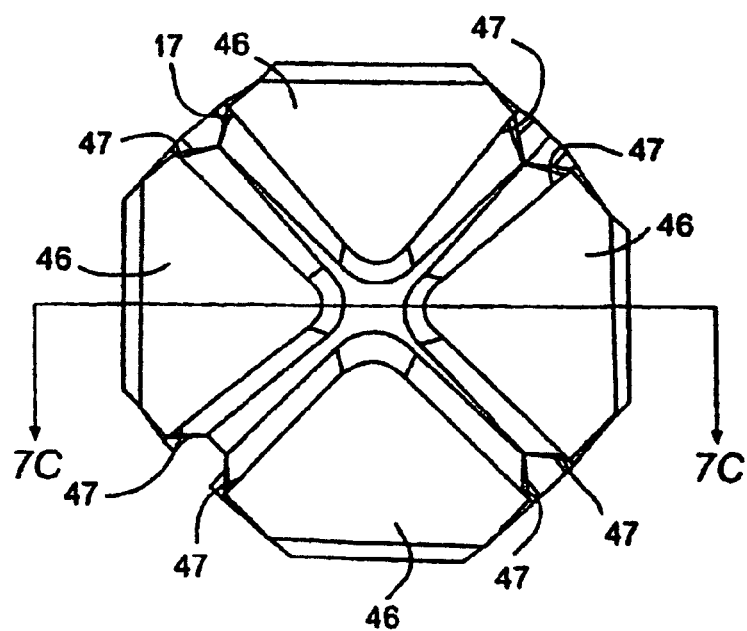
FIG. 7D is a top, end view of the end effector cutting mechanism of FIG. 7A.
Figure 8A:
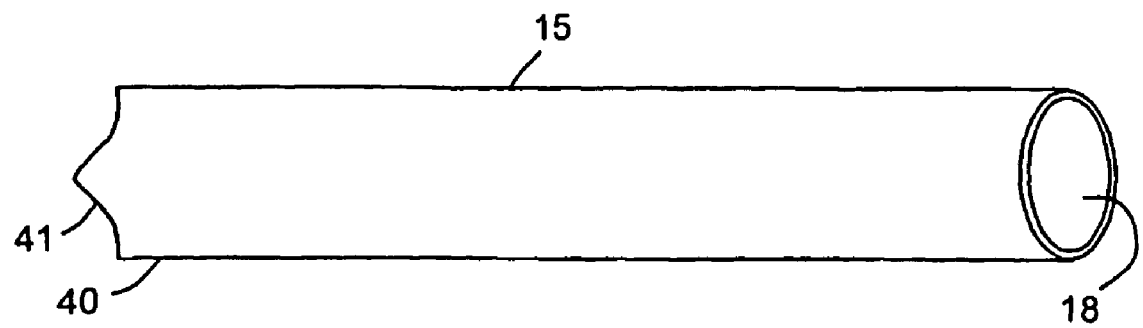
FIG. 8A is a side view of a needle portion of an end effector cutting mechanism according to the present invention.
Figure 8B:
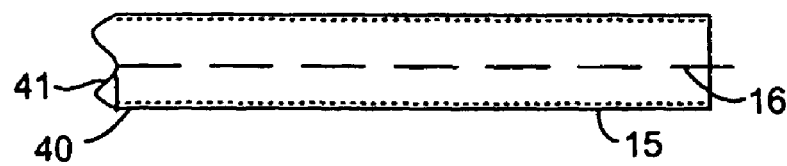
FIG. 8B is top view of the needle of FIG. 8A.
Figure 8C:
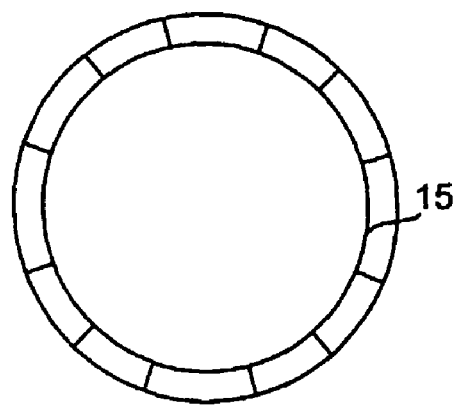
FIG. 8C is a cross-sectional end view of the needle of FIG. 8A.

As illustrated in FIG. 7C, needle 15 may be provided with a front hub 22, as well as rear hub 21, that act as a front stop and back stop limiting the movement of the cutting extension. Cutting extension 45 may be connected to or formed integrally with a float 30 slidably displacable between front stop 21 and back stop 22. When cutting extension 45 is in the retracted position wherein blades are biased outwardly on needle 15, hub or back stop 21 interacts with float 30 to limit the rearward travel of cutting extension 45. When cutting extension 45 is extended over needle 15, wherein blades 46 move inwardly over distal end 40 of needle 15, hub or front stop 22 limits the forward travel of cutting extension 45 relative to needle 15. By limiting the movement of the cutting extension, the stops prevent the cutting extension from being unnecessarily advanced into tissue beyond the distal end of needle 15 and retracted along the proximal end of needle 15 thereby creating a compact system despite any slack in the catheter assembly that allows for consistent sampling. It should be recognized that a float and front stop 22 could be used with the embodiments described in FIGS. 1-6.

Figure 10A:
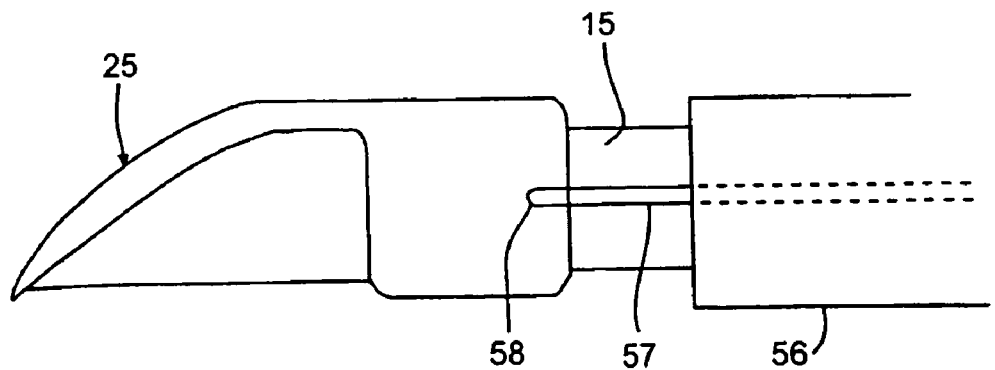
FIG. 10A is a side view of an end effector cutting mechanism attached to a tubular member.
Figure 10B:
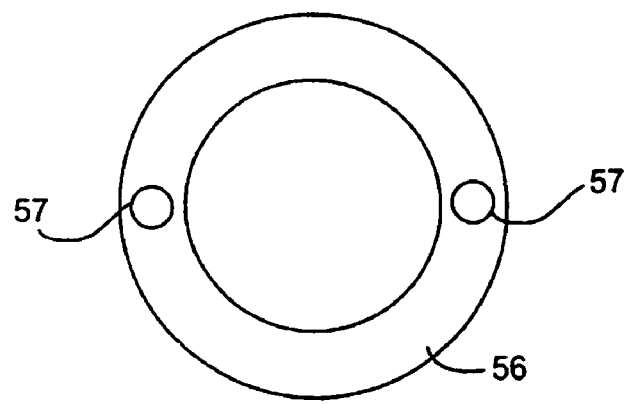
FIG. 10B is a cross-sectional end view of the tubular member of FIG. 10A.

Also in accordance with the present invention, tubular section 13 is provided to connect end effector assembly 14 to a handle assembly. As shown in FIGS. 2 and 12E, tubular section 13 includes a first tubular member 55 connecting needle 15 to handle assembly 12 and a second tubular member 56 coaxially disposed around first tubular member 55 connecting outer cutting mechanism 25 or 45 to handle assembly 12. First tubular member 55 may be connected to proximal end 23 of needle 15 through any suitable connection such as adhesives or a retaining ring. Alternatively, first tubular member 55 could be formed integrally with needle 15. Second tubular member 56 is preferably connected to float 30, connected to cutting mechanism 25 or 45 such that second tubular member 56 abuts the proximal end of the cutting mechanism. Alternatively, second tubular member 56 may be connected directly to the proximal end of cutting mechanism 25 or 45, as shown in FIG. 2. Second tubular member 56 may be connected to float 30 or the cutting mechanism through any suitable connection such as adhesives or a retaining ring. Second tubular member 56 may also be connected to float 30 or the cutting extension through connection wires 57 as shown in FIGS. 10A and 10B. Connection wires 57 may be placed in second tubular member 56 during extrusion of second tubular member. Distal ends 58 of connection wires 57 may be connected to outer cutting mechanism 25 or 45 through any suitable connector mechanism.

The second tubular member is preferably sized so as to pass through the working channel of an endoscope. The first tubular member is preferably sized so as to pass through the lumen of second tubular member and allow collection of and passage of biopsy tissue samples. First and second tubular members 55 and 56 are preferably flexible, such as flexible catheters, so that they may pass through the working channel of an endoscope or other delivery mechanism. First and second tubular members 55 and 56 may be made from polymer tubing, braided polymeric tubing, or other suitable material. While first and second tubular members are preferably flexible, the present invention is not limited to such and either one or both of the tubular members could be a rigid tubular member such as a trocar.

Handle assembly 12 is connected to the proximal ends of first and second tubular members 55 and 56 to allow relative movement between needle 15 and outer cutting mechanism 25 or 45 and to actuate the cutting extension. In accordance with an embodiment of the present invention as shown in FIGS. 11A-11F and 12A-12E, handle 12 includes a housing 60 having a distal end opening 61, a proximal end opening 62, a slot 63 on one surface of the housing, a notch 64, and an interior portion 65. Notch 64 is enlarged at one end 66.

Handle assembly 12 also includes a first hub 70, and a second hub 80. First hub 70 has an opening 71 at its proximal end, an opening 72 at its distal end, a body portion 73 in between, and an interior passageway 74. Body portion 73 of first hub 70 generally includes a first portion 76 sized to fit within the interior of second hub 80 and an enlarged second portion 77 adapted to grasped by a user. Second portion 77 includes a ridge 78 adapted to fit within notch 64 of housing 60. Ridge 78 has an enlarged end 79 such that it fits within enlarged end 66 of notch 64. First tubular member 55 may be connected to first hub 70 to provide communication between the interior of first tubular member 55 and needle 15 and to provide movement of first tubular member 55 and needle 15 when first hub 70 is moved. First tubular member 55 may connected to the interior passageway 74 through any suitable mechanism, such as by gluing or fastening means. First tubular member 55 may also be glued or fastened to the inside of proximal opening 71 of the first hub 70, or it may be fastened to the outside of proximal opening 71 through a retaining ring or cap or other mechanism.

Proximal opening 71 may be provided with a removable cap 75 to limit access to the interior of first tubular member 55 and needle 15. Proximal opening 71 may be connected to a source of aspiration or may provide access for other tools, such as a brush for brush cytology, thereby providing multiple sampling modalities.

Second hub 80 has a proximal end opening 81, a distal end opening 82, an opening 83 on one surface thereof and a hollow interior 84. Second tubular member 56 may be connected to distal end opening 82 such that the interior of second tubular member 56 communicates with the opening and that second tubular member 56 and cutting mechanism 25 or 45 are moved when second hub 80 is moved. FIG. 12E illustrates a preferred embodiment for attaching the second tubular member 56 to the handle assembly 12. Second tubular member 56 may be provided with a flared section 561. Flared section 561 may be positioned coaxially around distal end opening 82 so that flared section 561 rests on the outside of distal end opening 82. A tightener cap 562 may be placed over second tubular member 56 and positioned so that it rests on the flared section 561. Tightener cap 562, or other suitable retaining ring, may then be tightened to clamp the flared section 561 onto the outside of the distal end opening 82. It should be recognized that other suitable attachment mechanisms may be used.

Figure 11A:
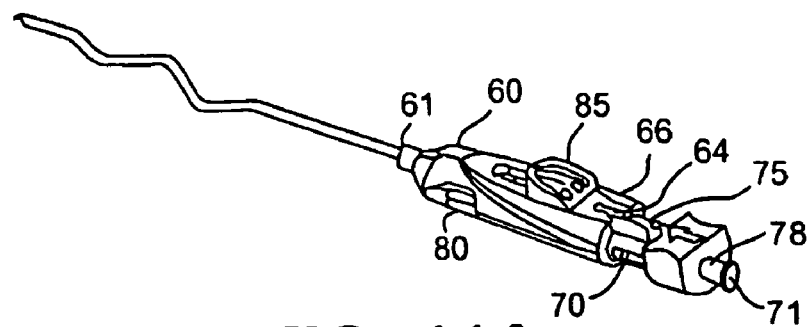
FIG. 11A is an elevational view of a handle assembly according to the present invention.
Figure 11B:
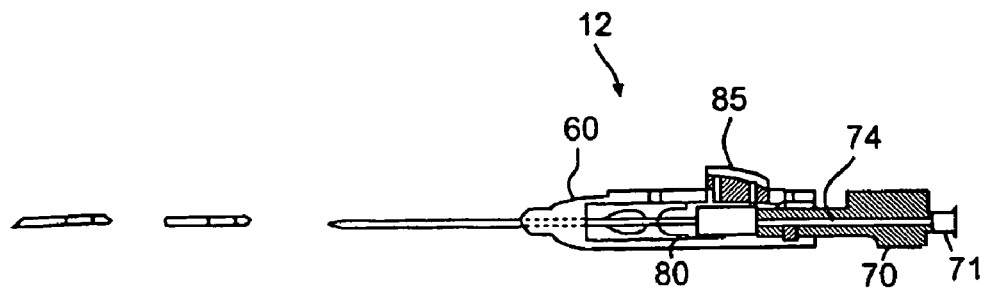
FIG. 11B is a sectional side view of the handle assembly of FIG. 11A.
Figure 11C:
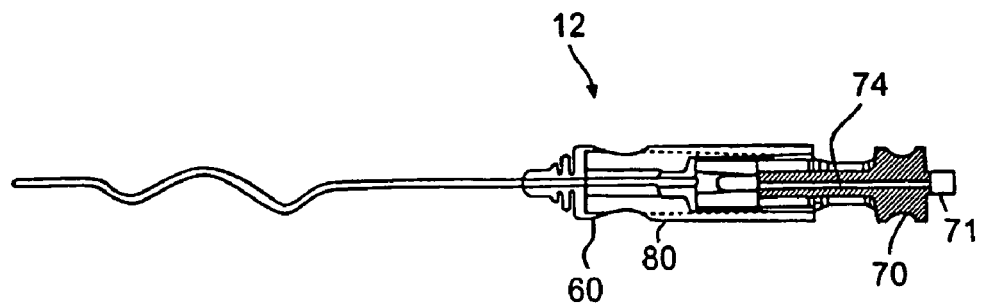
FIG. 11C is a sectional top view of the handle assembly of FIG. 11A.
Figure 11D:
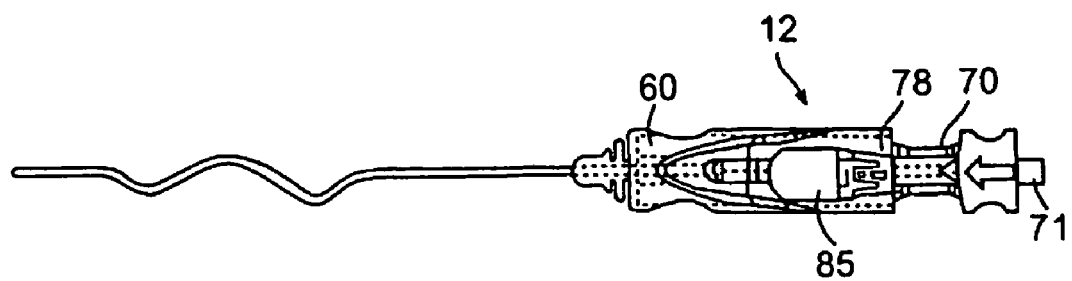
FIG. 11D is a top elevation view of the handle assembly of FIG. 11A.
Figure 11E:
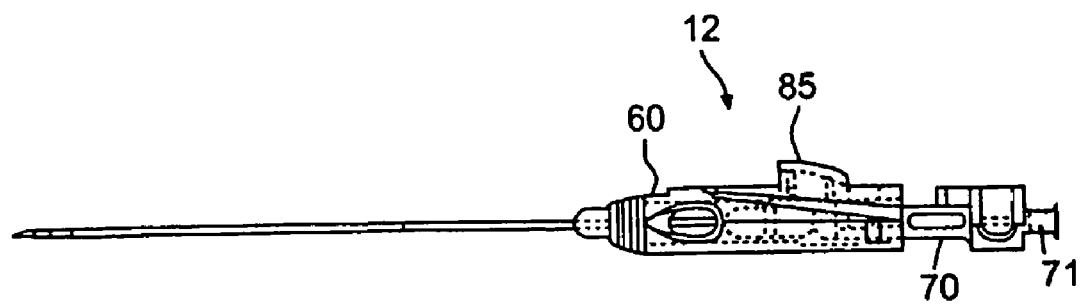
FIG. 11E is a side view of the handle assembly of FIG. 11A.
Figure 11F:
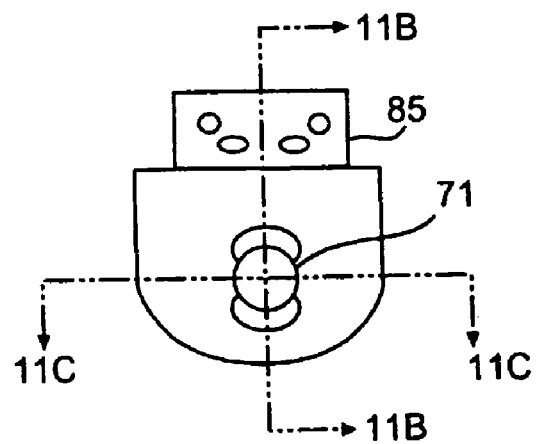
FIG. 11F is a bottom, end view of the handle assembly of FIG. 11A.
Figure 12A:
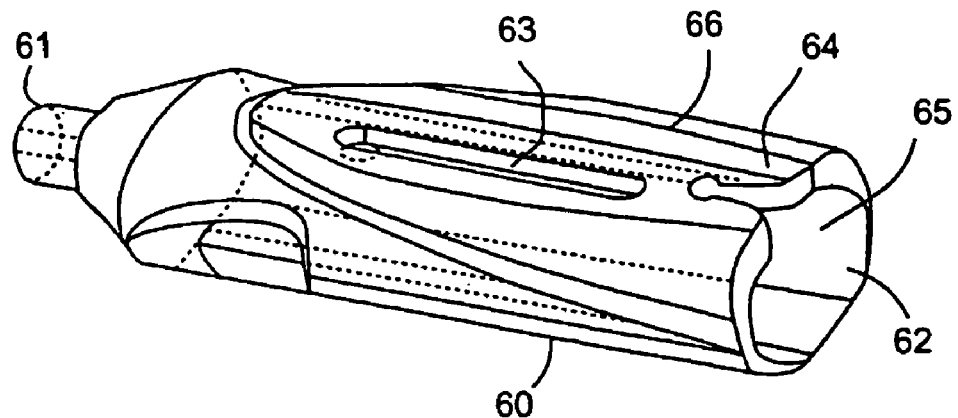
FIG. 12A is an elevational view of the housing portion of the handle assembly of FIG. 11A.
Figure 12B:
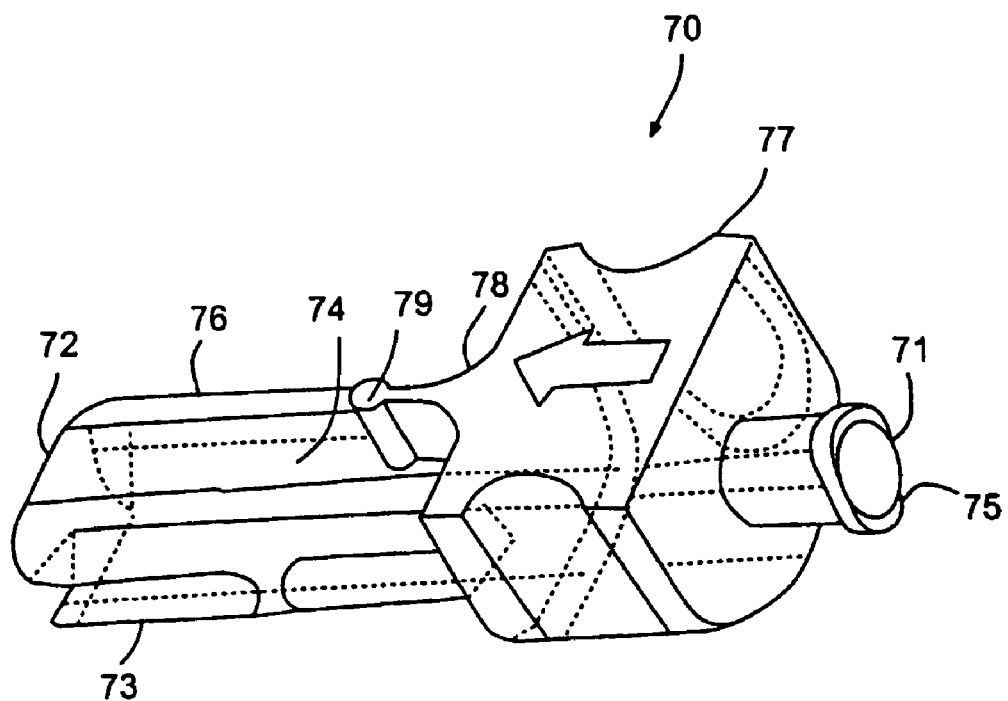
FIG. 12B is an elevation view of a first hub portion of the handle assembly of FIG. 11A.
Figure 12C:
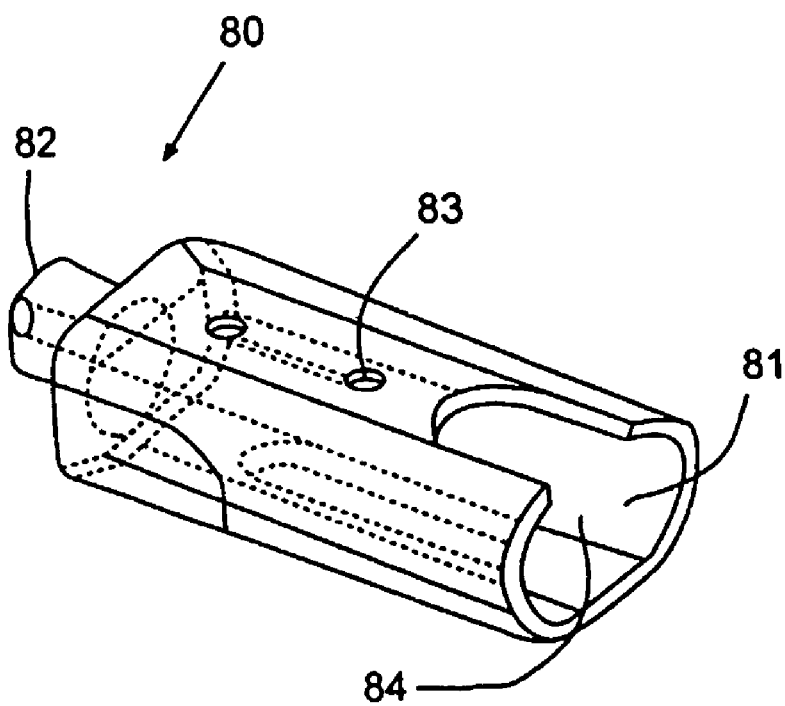
FIG. 12C is an elevational view of a second hub portion of the handle assembly of FIG. 11A.
Figure 12D:
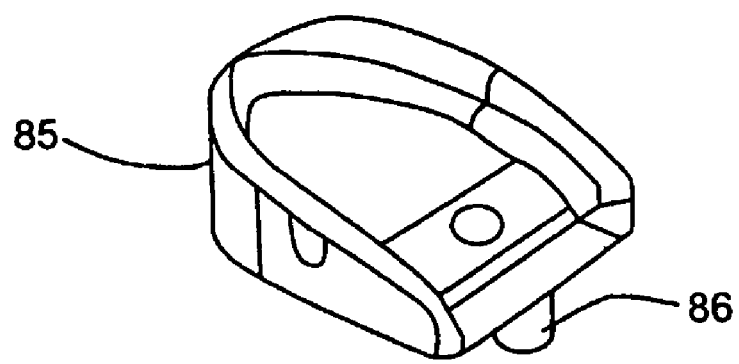
FIG. 12D is an elevational view of a tab portion of the handle assembly of FIG. 11A.
Figure 12E:
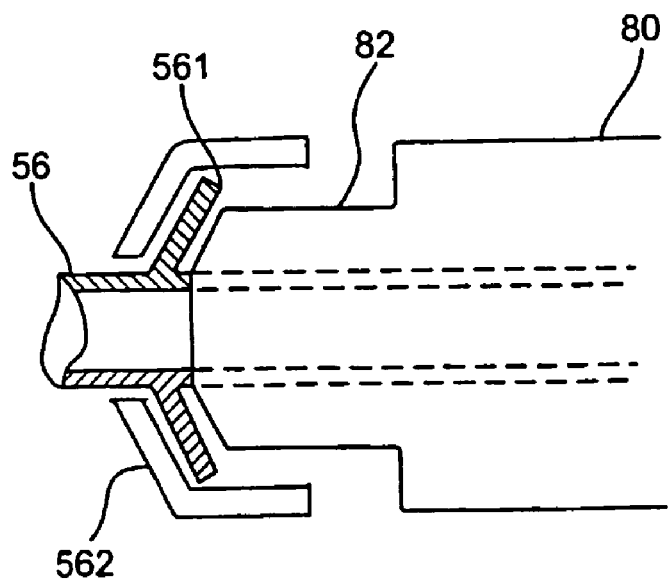
FIG. 12E is a cross-sectional side view of a mechanism for attaching a second tubular member to a second hub.

First portion 76 of first hub 70 is adapted to slidably fit within the hollow interior 84 of second hub 80 as shown by the arrow on enlarged portion 77 of first hub 70 in FIGS. 11D and 12B. Both first and second hubs 70 and 80 fit within housing 60 with enlarged portion 77 of first hub 70 extending from proximal opening 62 in housing 60.

Handle assembly 12 also includes a tab 85 having a pin 86 or other fastening means, such as a screw or some adhesive. Pin 86 of tab 85 is adapted to slidably fit within slot 63 of housing 60. Pin 86 also fits into opening 83 in second hub 80 to control movement of the second hub.

First and second tubular members 55 and 56 may be disposed in a housing tubular member, or third tubular member as described in connection with FIGS. 14A-14D, connected to housing 60. The housing tubular member may be retained on the distal end opening 61 of housing 60 with a retaining cap like the one described in FIG. 12E or it may be secured with other suitable retaining mechanisms.

In operation, a biopsy procedure may start with the needle in a retracted position in which enlarged portion 77 extends from housing 60 as shown. At this time cutting mechanism 25 is extended over needle 15 preventing tissue from entering the interior of needle 15. When a tissue sample is desire, enlarged portion 77 of first hub may be urged forward allowing ridge 78 to slide within notch 64 in housing 60 until ridge 78 meets the end of notch 64 causing needle 15 to be extended from cutting mechanism 25 thereby exposing needle 15 for entering a tissue site. Because notch 64 has a narrowing 66 surrounded enlarged opening 65, enlarged portion 79 of ridge 78 may be retained with notch 64. Ridge 78 can be dislodged from notch 64, but extra force is required to do so thereby preventing inadvertent withdrawal of needle 15. After needle 15 has penetrated the tissue site through a process in which the end effector is manually pushed into the tissue by advancing the tubular members, tab 85 may be slid forward within slot 63 causing cutting mechanism 25 or 45 to be extended over needle 15 thereby cutting and retaining the tissue sample within the interior of needle 15. This process may be repeated without removing needle 15 and cutting mechanism 25 and multiple full core samples of tissue may be obtained.

Figure 13:
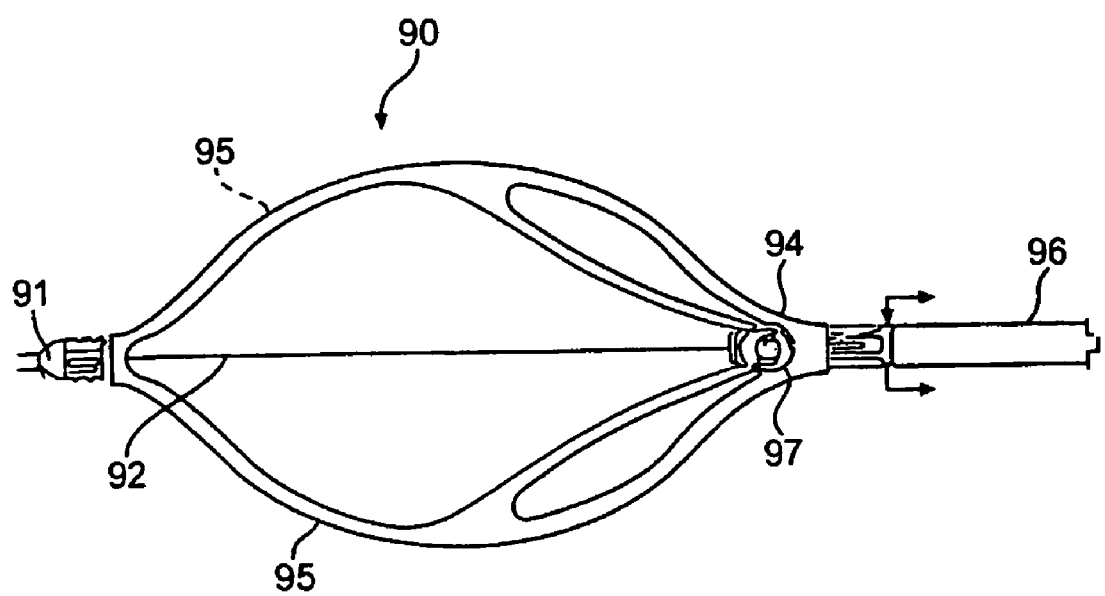
FIG. 13 is a handle assembly according to an embodiment of the present invention.

In accordance with another embodiment of the present invention, as shown in FIG. 13, handle 12 includes a resilient body portion 90 designed to fit within the hand of the operator and be compressed by the hand of the operator, providing a tactile handle responsive to pressure from the operator. Body portion 90 includes a distal end 91, a proximal end 96 and two side portions 95. Distal end 91 of body 90 is connected to the proximal end of second tubular member 56. A stabilization wire 92 is connected to the proximal end 96 of first tubular member 55 and the proximal end of body 90. Wire 92 may be fastened within an opening 97 in the proximal end of body 90 through a screw 94 or other suitable fastener. Alternatively, the first tubular member may extend through the body portion and proximal portion 96 of handle 12. When sides 95 of body 90 are compressed by the operator, second tubular member 56 and cutting mechanism 25 or 45 are extended. Needle 15 is retained in position relative to the proximal end of body 90 by wire 92 thereby allowing relative movement between cutting mechanism 25 or 45 and needle 15.

Figure 14A:
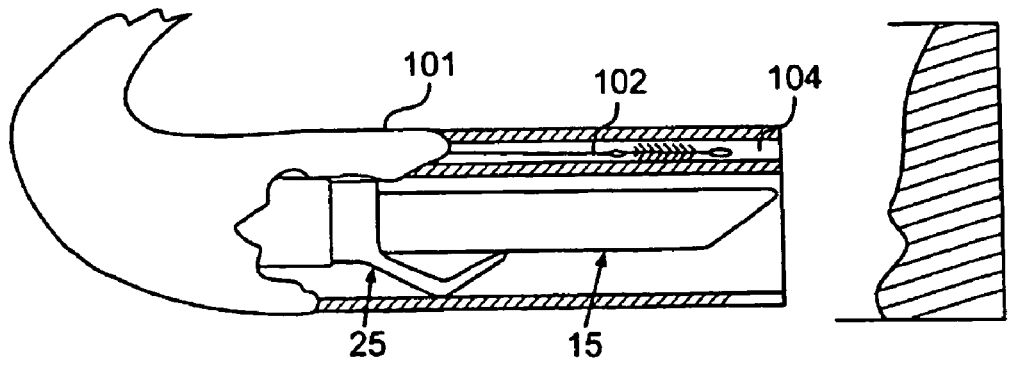
FIG. 14A is a partial sectional side view of an end effector, brush and tubular member according to the present invention.
Figure 14B:
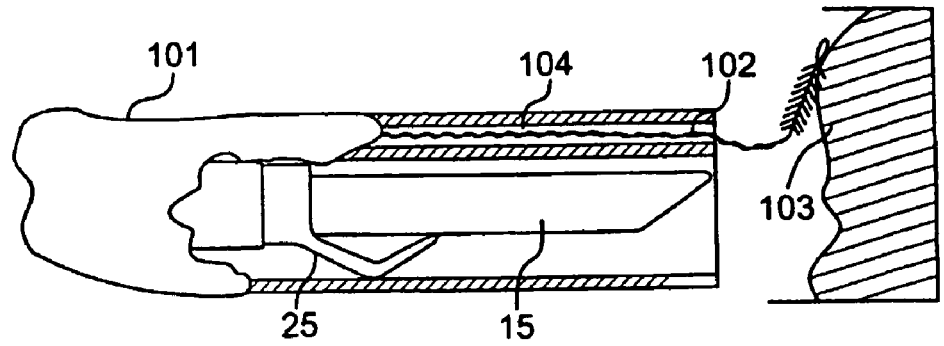
FIG. 14B is a partial sectional side view of the brush of FIG. 14A in use.
Figure 14C:
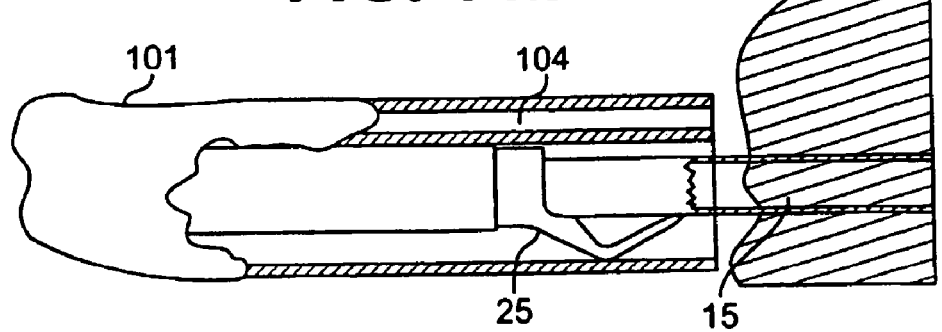
FIG. 14C is a partial sectional side view of the needle of the end effector cutting mechanism of FIG. 14A being inserted into a tissue site.
Figure 14D:
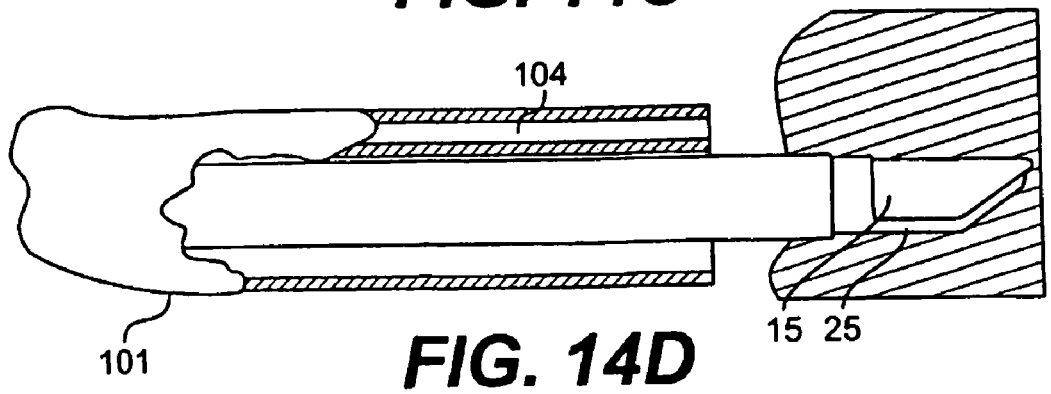
FIG. 14D is a partial sectional side view of the cutting extension of the end effector cutting mechanism of FIG. 14A extended over the needle.

As shown in FIGS. 14A-14D, the present invention may used within in a third tubular member 101, providing access for both the end effector cutting mechanism and a brush 102. Brush 102 may be used to obtain cell samples from a surface 103 of a tissue site as shown in FIG. 14B. The brush 102 may be disposed in a fourth tubular member 104 or alternatively may be disposed coaxially in the first tubular member 55. The operation of outer cutting mechanism 25 and needle 15 is also illustrated in FIGS. 14C and 14D. Outer cutting mechanism 25 is retracted from needle 15, and needle 15 is advanced into the tissue site to obtain a full core biopsy sample, as shown in FIG. 14C. Outer cutting mechanism 25 is then extended over needle 15, cutting the tissue within needle 15 and holding the tissue within the interior of needle 15, as shown in FIG. 14C. It should be recognized that this procedure could be repeated thereby obtaining multiple full core biopsy samples. It should also be recognized, as described above, that the brush 102 could be delivered to the site through the first tubular member and the needle 15 and that the handle 12 could be connected to a vacuum source to aspirate tissue through the needle 15.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A device for collecting body tissue comprising:
an inner member comprising a hollow portion to collect body tissue, the inner member having a distal end configured to both penetrate body tissue and define an opening of the hollow portion; and
an outer member co-axially and slidably disposed around an exterior of the inner member, the outer member comprising a distal end portion configured to penetrate body tissue, prevent body tissue from exiting the hollow portion of the inner member through the opening of the hollow portion, and allow the distal end of the inner member to extend beyond the distal end portion of the outer member,
wherein the opening of the hollow portion of the inner member is disposed in a plane that is not perpendicular to a longitudinal axis of the inner member, wherein a distalmost end of the outer member extends beyond the distalmost end of the inner member, and wherein the distalmost end of the outer member radially extends from one side of the inner member to a position beyond a longitudinal outer surface of a diametrically opposing side of the inner member to cover the entire opening of the hollow portion and close the opening.

2. The device of claim 1, wherein a first portion of the distal end portion is attached to a second portion of the distal end portion at one side of the opening.

3. The device of claim 1, wherein the distal end of the inner member has a distal facing surface, the distal end portion of the outer member lying flush against and distally to the distal facing surface of the distal end of the inner member so that a distalmost end of the inner member positionally coincides with a distalmost end of the outer member when the distal end portion of the outer member is positioned to prevent body tissue from exiting the hollow portion of the inner member.

4. The device of claim 1, wherein a portion of the distal end portion selectively covers the opening and is disposed in a plane that is not perpendicular to the longitudinal axis of the inner member.

5. The device of claim 1, wherein the distal end of the inner member has a distal facing surface, and a distalmost point of a first portion of the distal facing surface of the distal end of the inner member is disposed distal to a distalmost point of a second portion of the distal facing surface of the distal end of the inner member different from the first portion, the first and second portions of the distal facing surface being separated by the opening of the hollow portion of the inner member.

6. The device of claim 1, wherein the distal end portion includes only one flap that covers the entire opening of the hollow portion.

7. The device of claim 1, wherein the distal end of the inner member is slidably movable past the distal end portion of the outer member.

8. A device for collecting body tissue comprising:
   an inner member comprising a hollow portion to collect body tissue, the inner member having a distal end configured to both penetrate body tissue and define an opening of the hollow portion; and
   an outer member co-axially and slidably disposed around an exterior of the inner member, the outer member comprising a distal end portion configured to penetrate body tissue, prevent body tissue from exiting the hollow portion of the inner member through the opening of the hollow portion, and allow the distal end of the inner member to extend beyond the distal end portion of the outer member,
   wherein a first portion of the distal end portion radially extends beyond a longitudinal outer surface of the inner member defining a first side of the opening, covers the entire opening of the hollow portion to close the opening of the hollow portion, and is attached to a second portion of the distal end portion at only a second side of the opening, the second side of the opening being different from the first side of the opening.

9. The device of claim 8, wherein the distal end of the inner member has a distal facing surface, the distal end portion of the outer member lying flush against and distally to the distal facing surface of the distal end of the inner member so that a distalmost end of the inner member positionally coincides with a distalmost end of the outer member when the distal end portion of the outer member is positioned to prevent body tissue from exiting the hollow portion of the inner member.

10. The device of claim 8, wherein the first portion of the distal end portion is disposed in a plane that is not perpendicular to the longitudinal axis of the inner member.

11. The device of claim 8, wherein the distal end of the inner member has a distal facing surface, and a distalmost point of a first portion of the distal facing surface of the distal end of the inner member is disposed distal to a distalmost point of a second portion of the distal facing surface of the distal end of the inner member different from the first portion, the first and second portions of the distal facing surface being separated by the opening of the hollow portion of the inner member.

12. The device of claim 8, wherein the distal end portion includes only one flap that covers the entire opening of the hollow portion.

13. The device of claim 8, wherein the distal end of the inner member is slidably movable past the distal end portion of the outer member.

14. A device for collecting body tissue comprising:
   an inner member comprising a hollow portion to collect body tissue, the inner member having a distal end with a distal facing surface configured to both penetrate body tissue and define an opening of the hollow portion; and
   an outer member co-axially and slidably disposed around an exterior of the inner member, the outer member comprising a distal end portion configured to penetrate body tissue, prevent body tissue from exiting the hollow portion of the inner member through the opening of the hollow portion, and allow the distal end of the inner member to extend beyond the distal end portion of the outer member,
   wherein the distal end portion of the outer member lies flush against and distally to the distal facing surface of the distal end of the inner member so that a distalmost end of the inner member positionally coincides with a distalmost end of the outer member when the distal end portion of the outer member is positioned to prevent body tissue from exiting the hollow portion of the inner member.

15. The device of claim 14, wherein a portion of the distal end portion that covers the opening is disposed in a plane that is not perpendicular to the longitudinal axis of the inner member.

16. The device of claim 14, wherein a distalmost point of a first portion of the distal facing surface of the distal end of the inner member is disposed distal to a distalmost point of a second portion of the distal facing surface of the distal end of the inner member different from the first portion, the first and second portions of the distal facing surface being separated by the opening of the hollow portion of the inner member.

17. The device of claim 14, wherein the distal end portion includes only one flap that covers the entire opening of the hollow portion.

18. The device of claim 14, wherein the distal end of the inner member is slidably movable past the distal end portion of the outer member.

19. The device of claim 14, wherein the distalmost end of the outer member extends beyond the distalmost end of the inner member.

20. A device for collecting body tissue comprising:
   an inner member comprising a hollow portion to collect body tissue, the inner member having a distal end with a distal facing surface configured to both penetrate body tissue and define an opening of the hollow portion; and
   an outer member comprising a distal end portion configured to penetrate body tissue, prevent body tissue from exiting the hollow portion of the inner member through the opening of the hollow portion, and allow the distal end of the inner member to extend beyond the distal end portion of the outer member,
   wherein the distal end portion of the outer member defines an opening in communication with the opening of the hollow portion of the inner member, wherein a distalmost point of a first portion of the distal facing surface of the distal end of the inner member is disposed distal to a distalmost point of a second portion of the distal facing surface of the distal end of the inner member different from the first portion, the first and second portions of the distal facing surface being separated by the opening of the hollow portion of the inner member, and wherein the distal end portion of outer member lies flush against and distally to the distal facing surface of the inner member so that a distalmost end of the inner member positionally coincides with a distalmost end of the outer member.

21. The device of claim 20, wherein, upon retraction of the distal end portion of outer member, the outer member cuts body tissue at the distal facing surface of the inner member and prevents body tissue from exiting the hollow portion of the inner member.

22. The device of claim 20, wherein a portion of the distal end portion selectively covers the opening of the hollow portion and is disposed in a plane that is not perpendicular to the longitudinal axis of the inner member.

23. The device of claim 20, wherein the distal end of the inner member is slidably moveable past the distal end portion of the outer member.

24. The device of claim 20, wherein the outer member is co-axially and slidably disposed around an exterior of the inner member.

* * * * *